United States Patent
Freeman et al.

(10) Patent No.: US 7,037,335 B2
(45) Date of Patent: May 2, 2006

(54) BULBOUS SCLERAL IMPLANTS FOR THE TREATMENT OF EYE DISORDERS SUCH AS PRESBYOPIA AND GLAUCOMA

(75) Inventors: Jerre M. Freeman, Memphis, TN (US); Richard W. Mendius, Collierville, TN (US)

(73) Assignee: Eagle Vision, Inc., Memphis, TN (US)

( * ) Notice: Subject to any disclaimer, the term of this patent is extended or adjusted under 35 U.S.C. 154(b) by 245 days.

(21) Appl. No.: 10/299,671

(22) Filed: Nov. 19, 2002

(65) Prior Publication Data

US 2004/0098123 A1     May 20, 2004

(51) Int. Cl.
*A61F 2/14* (2006.01)
(52) U.S. Cl. ........................................ 623/4.1
(58) Field of Classification Search ............... 623/4.1, 623/6.14, 6.64; 600/398, 558
See application file for complete search history.

(56) References Cited

U.S. PATENT DOCUMENTS

| | | | |
|---|---|---|---|
| 2,952,023 A | 9/1960 | Rosen | 3/13 |
| 3,064,643 A | 11/1962 | Dixon | 128/76.5 |
| 3,454,966 A | 7/1969 | Rosen | 3/13 |
| 5,005,577 A * | 4/1991 | Frenkel | 600/398 |
| 5,489,299 A | 2/1996 | Schachar | 623/4 |
| 5,520,631 A | 5/1996 | Nordquist et al. | 604/8 |
| 5,558,630 A | 9/1996 | Fisher | 604/8 |
| RE35,390 E | 12/1996 | Smith | 604/8 |
| 5,704,907 A | 1/1998 | Nordquist et al. | 604/8 |
| 5,824,086 A * | 10/1998 | Silvestrini | 623/5.11 |
| 6,079,417 A | 6/2000 | Fugo | 128/898 |
| 6,117,170 A | 9/2000 | Batdorf, Sr. | 623/4 |
| 6,138,307 A | 10/2000 | McDonald | 6/5.11 |
| 6,193,656 B1 | 2/2001 | Jeffries | 600/398 |
| 6,197,056 B1 | 3/2001 | Schachar | 623/4.1 |
| 6,206,919 B1 | 3/2001 | Lee | 623/5.12 |
| 6,280,468 B1 | 8/2001 | Schachar | 623/4.1 |
| 6,299,640 B1 | 10/2001 | Schachar | 623/4.1 |
| 6,470,212 B1 | 10/2002 | Weijand et al. | 607/35 |

(Continued)

FOREIGN PATENT DOCUMENTS

DE     44 38 201 A1 *  5/1996

(Continued)

OTHER PUBLICATIONS

*Scleral Expansion Bands Still Rooted in Controversy*, by Michela Cimberle, Ocular Surgery News, Feb. 1, 2003.

(Continued)

*Primary Examiner*—David H. Willse
(74) *Attorney, Agent, or Firm*—Gordon & Jacobson, PC (57) ABSTRACT

Scleral implants are provided having structure that locks the implant into incisions in the sclera and provide a stress thereto. In several embodiments, such structure includes a foot that extends laterally from a bottom of the implant, as well as an opening through which suture may be passed. Furthermore, the foot of the implant may be contoured to conform to the natural curvature of the sclera. In other embodiments, the implant is generally disc-shaped and includes a tab and a suture opening. With this implant, one or two pockets are defined in the sclera, preferably at eleven o'clock and/or one o'clock, the implant is placed therein, and the pocket incision may be closed with suture. The implant may also include a system for measuring and transmitting the intraocular pressure. With all the implants, the eye pressure is increased and/or the sclera is lifted to treat a disorder of the eye.

13 Claims, 6 Drawing Sheets

U.S. PATENT DOCUMENTS 6,475,170 B1 * 11/2002 Doron et al. ............... 600/587
2003/0078487 A1 * 4/2003 Jeffries et al. .............. 600/398

FOREIGN PATENT DOCUMENTS

DE 198 58 172 A1 * 6/2000

OTHER PUBLICATIONS

*New Surgery for Presbyopia May be on the Horizon,* by Lou Koury, Ocular Surgery News.
*Anterior Ciliary Sclerotomy with Silicone Expansion Plug Implantation (ACS-SEP),* by Hideharu Fukasaku, M.D., A.S.C.R.S. Course No 1107: "Presbyopia: Is surgery able to compensate for loss of accommodation?", Jun. 1, 2002.
*Surgical treatment of Presbyopia,* by George D. Baikoff, A.A.O. Orlando Course No 652: Presbyopia: Is surgery able to compensate for loss of accommodation?, Oct. 23, 2002.
*Reading Implants May Restore Accommodation,* by Diane Angelucci, EyeWorld, Jun. 02.
*Atlas of Refractive Surgery,* by Benjamin F. Boyd, English Edition, 2000, D'vinni Editorial Ltda., Bogota Colombia.

* cited by examiner

BULBOUS SCLERAL IMPLANTS FOR THE TREATMENT OF EYE DISORDERS SUCH AS PRESBYOPIA AND GLAUCOMA

BACKGROUND OF THE INVENTION

1. Field of the Invention

This invention relates broadly to prostheses. More particularly, this invention relates to eye prostheses for improving vision and methods of use of such prostheses for the treatment of disorders of the eye.

2. State of the Art

The human eye generally comprises a cornea, an iris, a ciliary body (muscle), a capsular bag having an anterior wall and a posterior wall, and a natural crystalline lens contained within the walls of the capsular bag. The capsular bag is connected to the ciliary body by means of a plurality of zonules which are strands or fibers. The ciliary body surrounds the capsular bag and lens, defining an open space, the diameter of which depends upon the state (relaxed or contracted) of the ciliary body.

When the ciliary body relaxes, the diameter of the opening increases, and the zonules are pulled taut and exert a tensile force on the anterior and posterior walls of the capsular bag, tending to flatten it. As a consequence, the lens is also flattened, thereby undergoing a decrease in focusing power. This is the condition for normal distance viewing. Thus, the emmetropic human eye is naturally focused on distant objects.

Through a process termed accomodation, the human eye can increase its focusing power and bring into focus objects at near. Accomodation is enabled by a changes in the anatomy, particularly including the relationship between the lens, zonules and ciliary body. According to the generally accepted Helmholtz theory of accomodation, when the ciliary body contracts, the diameter of the opening is decreased thereby causing a compensatory relaxation of the zonules. This in turn removes or decreases the tension on the capsular bag, and allows the lens to assume a more rounded or spherical shape. This rounded shape increases the focal power of the lens such that the lens focuses on objects at near.

As such, the process of accommodation is made more efficient by the interplay between stresses in the ciliary body and the lens. When the ciliary body relaxes and reduces its internal stress, there is a compensatory transfer of this stress into the body of the lens, which is then stretched away from its globular relaxed state into a more stressed elongated conformation for distance viewing. The opposite happens as accommodation occurs for near vision, where the stress is transferred from the elongated lens into the contracted ciliary body.

As humans age, there is a general loss of ability to accommodate, termed "presbyopia", which eventually leaves the eye unable to focus on near objects. According to conventional theory, this loss in ability to focus on near objects is a consequence of a loss in elasticity of the lens capsule and/or sclerosis of the lens with age. Consequently, even though the radial tension of the zonules is relaxed by contraction of the ciliary bodies, the lens fails to assume a greater curvature.

Figure 1:
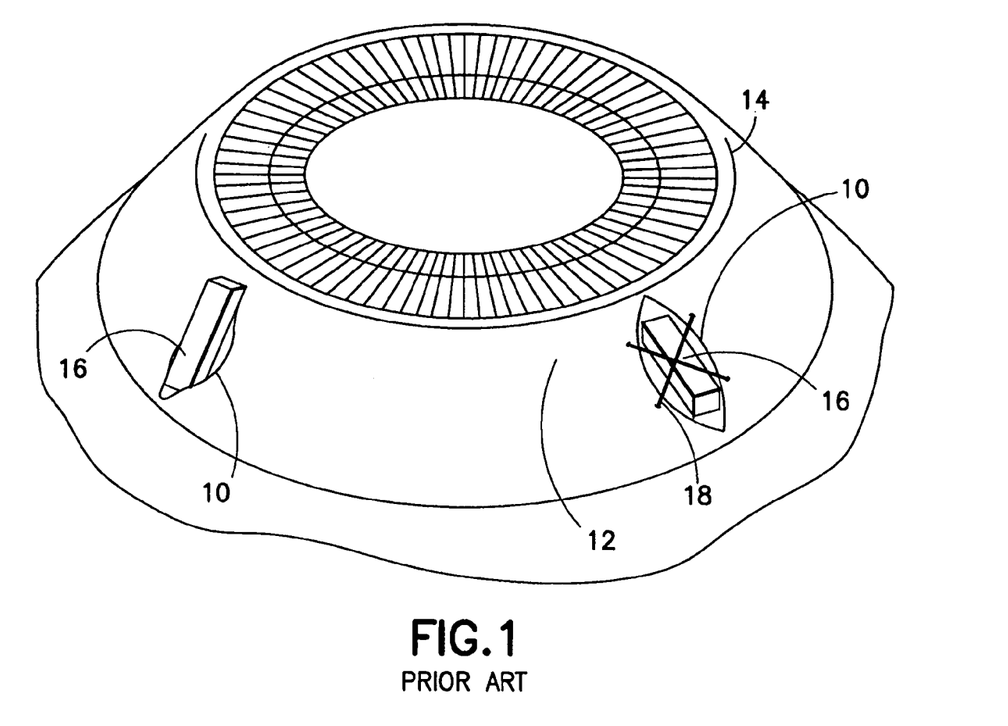
FIG. 1 illustrates the procedure described by Dr. Hideharu Fukasaku.
Figure 2:
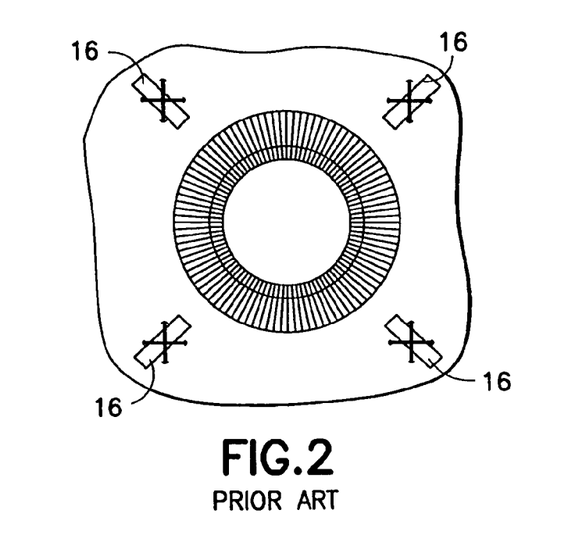
FIG. 2 shows scleral implants implanted according to the procedure shown in FIG. 1.
Figure 3:
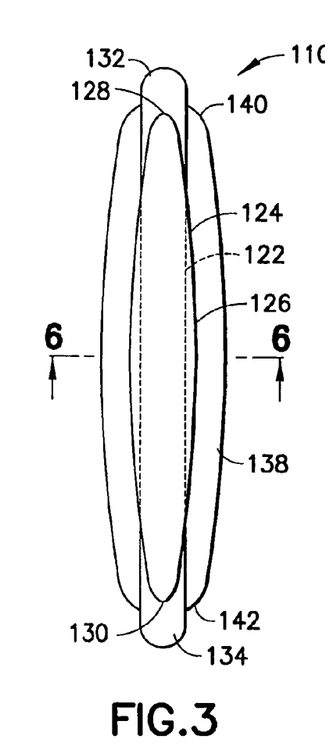
FIG. 3 is a plan view of a scleral implant according to a first embodiment of the invention.
Figure 4:
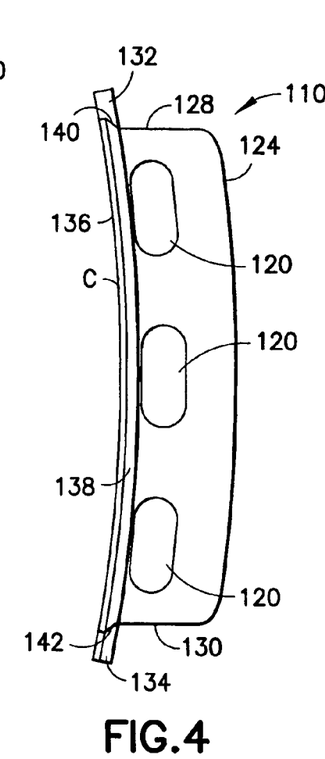
FIG. 4 is a side elevation of the scleral implant of FIG. 3.
Figure 5:
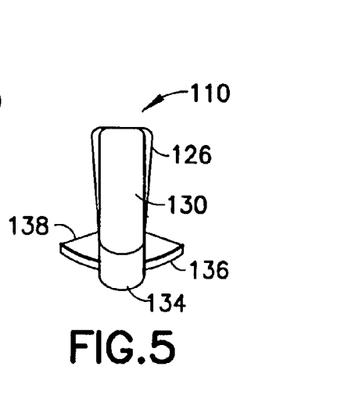
FIG. 5 is an end view of the scleral implant of FIG. 3.
Figure 6:
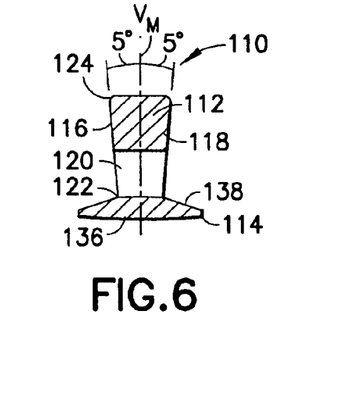
FIG. 6 is a cross-section across line 6—6 in FIG. 3.

Hideharu Fukasaku, M.D., has developed a procedure for the treatment of presbyopia, described in *Anterior Ciliary Sclerotomy with Silicone Expansion Plug Implantation (ACS-SEP)*, Handout for A.S.C.R.S. Course No. 1107: Presbyopia: Is Surgery Able to Compensate for Loss of Accommodation? (Jun. 1, 2002). Referring to prior art FIGS. 1 and 2, in the procedure, deep radial incisions (limbal peritomies) 10 are made in four oblique quadrants of the sclera 12 over the ciliary body and between the insertions of the four main extraocular muscles. The incisions 10 are each approximately 3 mm in length and at 90% depth. Each incision 10 is started at about 1 mm from the corneal surgical limbus 14 and extends 3 mm radially from that location. Lateral pockets (not shown) are preferably defined at the full depth of the incisions, and each pocket is spread with a forceps. A small hand-cut length of a silicone rod (plug) 16 is implanted into each incision. The conjunctiva is then draped over the incision sites, and the sides of each incision are secured with an absorbable suture 18. The purpose of sewing the silicone implant into the incision is to maintain the effect of making the incision. In fact, making the incision alone tends to help people read at near distance, but this effect diminishes within several months. The implant 16 appears to be a barrier that prevents the scleral tissue from healing, reapproximating and closing the incision, thus maintaining the effect of the incisions.

One theory suggesting why the Fukasaku method increases near distance vision, and thus provides a treatment for presbyopia, is that making the incisions lengthens the circumference of the sclera across the incision, thus providing additional space inside the eye for the ciliary body to contract and cause more effect upon the crystalline lens. If this theory is correct, sewing the silicone implants into their respective incisions increases the effect of creating room for the ciliary body to expand.

An alternate theory suggests that sewing the silicone implants into the incisions places additional pressure on the internal structures of the eye. This causes an increased pressure on the vitreous body to push on the crystalline lens, thus moving it forward which increases the optical effect of the ciliary body. That is, the internal dynamics of the eye are sufficiently altered to at least partially reverse the effects of presbyopia.

While the Fukasaku procedure has merit, the hand-cut silicone implants require physician time to prepare and, due to their hand-cut nature, are inconsistent in length and even shape. Moreover, the shape of the implants is not ideal for secure implantation in the sclera and for providing the desired stress on the sclera.

Spencer Thornton, M.D., and Jim Hayes, M.D., have developed a pre-manufactured titanium implant that can be used in place of Fukasaku's hand-cut silicone plugs. The uniform implants have an inverted T-shape in which the laterally extending portions are intended to seat within the lateral pockets of the incision described by Fukasaku. Initial results suggest that such implants permit more uniform results when using the Fukasaku methodology. However, the Thornton implants are not ideally shaped for scleral implantation, and may be expelled by the sclera.

Ronald Schacher, M.D., has also proposed several other concepts for scleral implants. See, for example, U.S. Pat. Nos. 5,489,299, 6,197,056, and 6,299,640, which are incorporated by reference herein in their entireties. While Schacher proposes a theory as to why presbyopia correction occurs which is contrary to the conventional Helmholtz theory, it appears the Schacher implants may provide the same function as the others (regardless of which theory is correct). Nevertheless, the Schacher implants are subject to the same limitations as other premanufactured scleral implants.

SUMMARY OF THE INVENTION

It is therefore an object of the invention to provide scleral implants which when implanted in the sclera provide a treatment for one or more eye disorders.

It is another object of the invention to provide scleral implants that are adapted to alter the stress on the sclera.

It is a further object of the invention to provide ophthalmic implants that are configured to possibly increase the volume of the eye when implanted in the sclera.

It is an additional object of the invention to provide ophthalmic implants that increase the pressure within the vitreous cavity, thereby possibly causing the lens to move forward.

It is also an object of the invention to provide scleral implants that are better retained at the sclera.

It is yet a further object of the invention to provide scleral implants that include structure that facilitates the implantation procedure.

It is still another object of the invention to provide implants that are adapted to provide a treatment for presbyopia and glaucoma when implanted in the sclera.

It is still a further object of the invention to provide a method of treatment for eye disorders.

In accord with these objects, which will be discussed in detail below, several scleral implants are provided. According to one embodiment of the invention, an elongate implant is provided having a preferably inverted T-shape cross-section, as well as additional structure adapted to lock the implant into incisions in the sclera. Such structure includes a foot that extends laterally from a bottom portion of the implant in all peripheral directions, as well as an opening through which suture may be passed. Furthermore, the foot of the implant has a lower surface contoured to curve in preferably two directions. The contour of the foot may provide one or more of the following ophthalmic effects: (1) conformation of the foot to the natural curvature of the sclera, (2) volumetric expansion of the eye to define additional space for movement of the ciliary body, (3) an increase in pressure in the vitreous space, (4) a change the relationships of the anatomy, (5) an improvement in accommodation, (6) an improvement in the ability to see small objects at near; i.e., reading is facilitated, (7) a tilting of the lens, and/or (8) inducement of astigmatism. Also in accord with the invention, the elongate implants may define various other cross-sectional shapes, e.g., V-shaped or rectangular, that are also suitable for insertion into an incision and providing the desired ophthalmic effect.

Implants having structures in accord with the above embodiments are implanted in scleral incisions generally in accord with the procedure defined by Fukasaku, but additionally secured in the incisions by the shape and structure thereof. That is, with respect to each implant, the foot of the implant projects in all directions into an undercut of the scleral incision, including at the ends of the implant. Alternatively, no undercut is made, and the foot projects into the scleral tissue along the sides of the incision. In addition, suture is passed through both the opening in the implant and the scleral tissue and tied. As such, these structures and the utilization thereof operate to secure the implant in the incision between the edges of the incision. While the implant thus serves as a tissue barrier preventing the edges of the scleral incision from coapting, the mulitdirectional curvature along the bottom of the base permits the volume of the eye to be altered for a desired volumetric expansion or other opthalmic effect.

According to another embodiment of the scleral implant, the implant is generally disc-shaped or teardrop-shaped, and preferably includes a tab defining an opening for suture. In accord with a preferred method of implantation of the implants, two short straight or slightly curved incisions mad along an upper portion of the sclera, e.g., at eleven o'clock and one o'clock. Dissecting away from the twelve o'clock position, pockets are defined and the implants are provided therein and locked therein with suture passed through the suture opening in the tab as well as the scleral tissue. Moreover, an embodiment is provided that is suitable for use without suture. The implanted implants may provide similar opthalmic effects to elongate opthalmic implant. That is, (1) volumetric expansion of the eye to define additional space for movement of the ciliary body, (2) an increase in pressure in the vitreous space, (3) a change in the relationships of the anatomy, (4) an improvement in accomodation, (5) an improvement in the ability to see small objects at near; i.e., reading is facilitated, (6) a tilting of the lens, and/or (7) inducement of astigmatism may be provided.

Additional objects and advantages of the invention will become apparent to those skilled in the art upon reference to the detailed description taken in conjunction with the provided figures.

BRIEF DESCRIPTION OF THE DRAWINGS

Prior art

Prior art

DETAILED DESCRIPTION OF THE PREFERRED EMBODIMENTS

Turning now to FIGS. 3 through 6, an implant 110 according to a first embodiment of the invention is shown. The implant 110 includes an elongate body 112 and a foot 114 that is transverse to the body 112. The body 112 includes lateral walls 116, 118 that are angled away from a cross-sectional vertical midline $V_M$, preferably by approximately 5°. A central portion of the body 112 preferably also defines at least one (three shown) preferably oblong hole 120. The lower portion 122 of the body 112 preferably has a substantially uniform thickness along a majority of its length, while the upper end 124 of the body is thickest at a midpoint 126 of the length, and tapers toward the ends 128, 130 of the body. The foot 114 preferably extends about an entirety of the body 112, particularly including the ends 128, 130 of the body. In addition, the ends 128, 130 of the foot 114 are provided with extensions 132, 134. According to the first embodiment, a lower surface 136 of the foot 114 is preferably curved along concave curve C in the direction of the length of the implant 110. An upper surface 138 of the foot 114 is preferably angled downward toward the lower surface 136.

The implant 110 is made from a biocompatible material, such as a metal or metal alloy such as titanium or stainless steel. For one size of an implant 110, the implant generally has a length of approximately 2.0 to 3.5 mm, a width across the base 112 of approximately 0.10 to 0.4 mm, a width across the foot 114 of approximately 0.35 to 0.75 mm, and a height from the lower surface 136 of the foot to the upper end 124 of the base of approximately 0.45 to 0.75 mm. While it is preferred that the length of the implant remain within the above exemplar range, it is appreciated that the implant may be provided in several discrete sizes, with, e.g., a maximum width across the base 110 of 0.4, 0.6, and 0.8 mm and a corresponding range of sizes for the width across the foot 114 and the height of the implant.

In accord with one method of the invention, incisions are generally made and located in accord with the procedure defined by Fukasaku; i.e., in each of four quadrants of the sclera. The incisions are preferably no longer than the length of the body 112; i.e., they do not extend the length of the foot 114. A lateral undercut is preferably also provided to the incisions. The implants 110 are then inserted into the incisions. Curve C along the lower surface 136 of the foot 114 permits the implant to overlie the sclera in accord with the anatomical shape of the surface of the sclera. When the foot is positioned into the lateral undercut, the ends 140, 142 of the foot 114 as well as the extensions 132, 134 are burrowed into the tissue at the ends of the incision. Optionally, an additional undercut is provided at the ends of the incision to receive the extensions 132, 134. After an implant is desirably seated in the incision, suture is passed through tissue on one side of the incision, through at least one hole 120 in the body 112, and out the tissue on the other side of the incision. Where two or more holes are provided with suture, the implant may be better stabilized, as suture through a single hole may cause the implant to pivot about the suture point. The suture is then tied to secure the implant 110 within the incision. The holes 120, in addition to providing a space for receiving suture, permit potential tissue ingrowth that may operate to anchor the implant. This is in contrast to the Fukasaku methodology, discussed above, in which suture is passed between the sides of the incision, but cannot be passed through the implant, and in which no tissue ingrowth is permitted. The ends 140, 142 of the foot, the extensions 132, 134, and the suture opening 120 (and suture therethrough), all operate to secure the implant in the incision between the edges of the incision. The implant thus serves as a uniform and securely held tissue barrier preventing the edges of the scleral incision from coapting. In addition, the curvature along the bottom of the foot conforms to the shape of the eye in the radial direction. Furthermore, the implant may permit the volume of the eye to be altered via manipulation of the tissue about the implant to effect a desired volumetric expansion of the eye that may define additional space for movement of the ciliary body, may cause an increase in pressure in the vitreous space, may change the relationships of the anatomy, may improve accommodation, may improve the ability to see small objects at near (e.g. reading may be facilitated), may cause a beneficial tilting of the lens, and/or may induce a degree of astigmatism.

Figure 7:
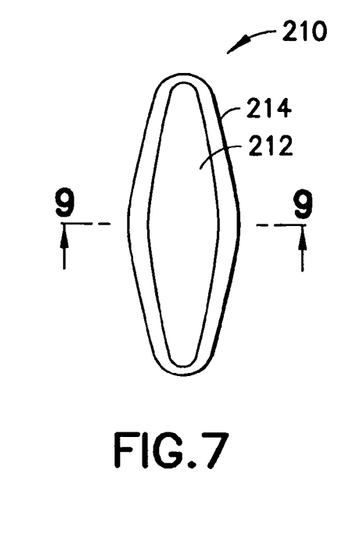
FIG. 7 is a top view of a second embodiment of a scleral implant according to the invention.
Figure 8:
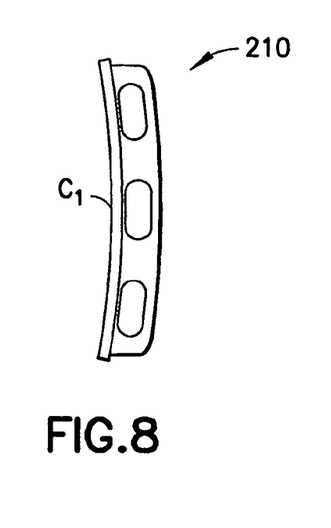
FIG. 8 is a side elevation of the scleral implant of FIG. 7.
Figure 9:
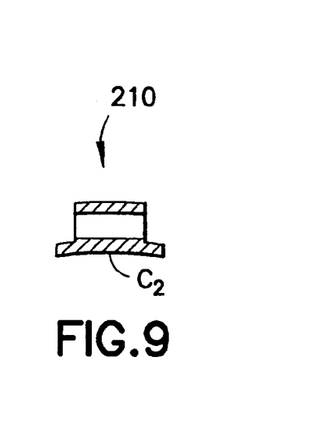
FIG. 9 is a cross-section of the scleral implant of FIG. 7 across line 9—9.

Turning now to FIGS. 7 through 9, a second embodiment of an implant 210 according to the invention, substantially similar to the first embodiment 110 (with like elements having reference numerals incremented by 100), is shown. Implant 210 has a body 212 which has a relatively thick central portion and which tapers toward end portions. At each location along the length of the implant 210, the thickness of the body 212 is substantially the same at upper and lower portions. In addition, the lower surface 236 is curved in two directions: a first concave curve $C_1$ along a length of the foot, and a second concave curve $C_2$ perpendicular to curve $C_1$. The foot 214 preferably extends a fixed distance, e.g., 0.15 mm, from each point about a periphery of the body 212.

Figure 10:
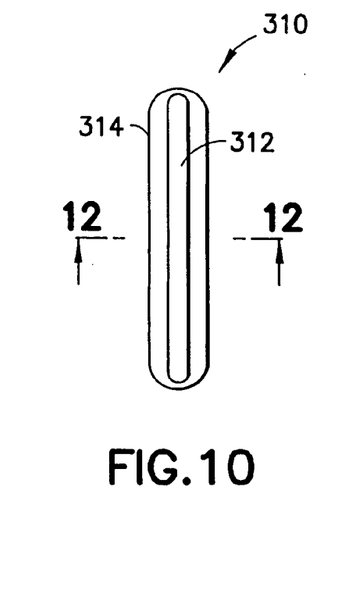
FIG. 10 is a top view of a third embodiment of a scleral implant according to the invention.
Figure 11:
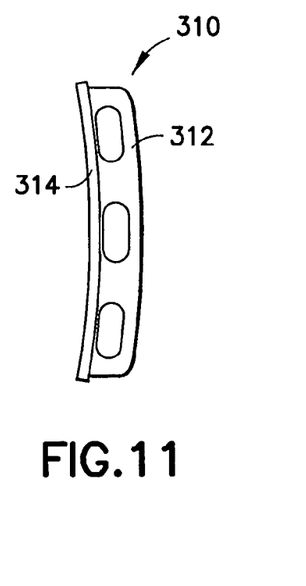
FIG. 11 is a side elevation of the scleral implant of FIG. 10.
Figure 12:
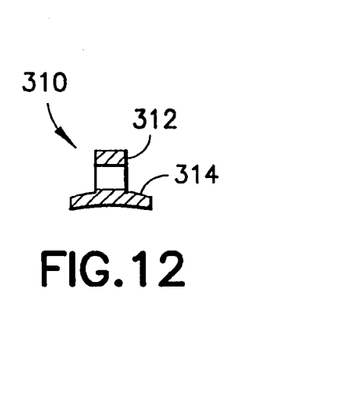
FIG. 12 is a cross-section of the scleral implant of FIG. 10 across line 12—12.

Referring to FIGS. 10 through 12, a third embodiment of an implant 310 according to the invention, substantially similar to the second embodiment 210 (with like elements having reference numerals incremented by 100 relative thereto), is shown. Implant 310 has a body 312 of substantially uniform thickness along its length, and a foot 314.

Figure 13:
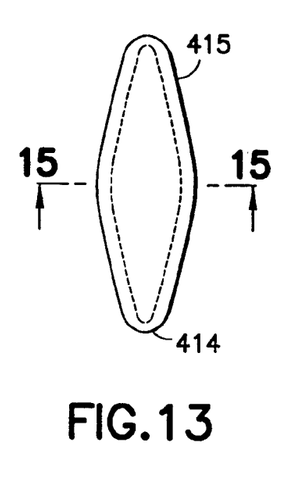
FIG. 13 is a top view of a fourth embodiment of a scleral implant according to the invention.
Figure 14:
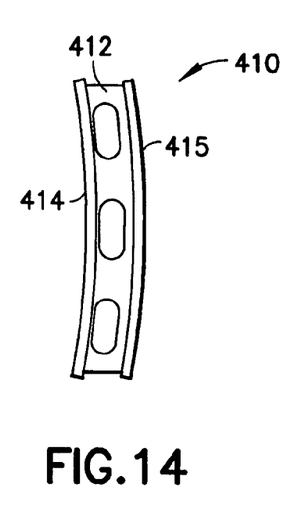
FIG. 14 is a side elevation of the scleral implant of FIG. 13.
Figure 15:
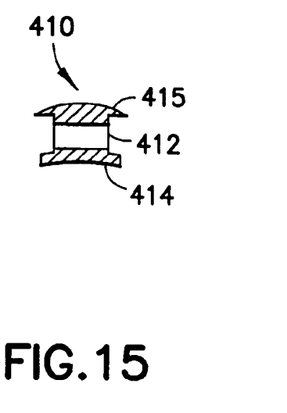
FIG. 15 is a cross-section of the scleral implant of FIG. 13 across line 15—15.

Referring to FIGS. 13 through 15, a fourth embodiment of an implant 410 according to the invention, substantially similar to the second embodiment 210 (with like elements having reference numerals incremented by 200 relative thereto), is shown. Implant 410 has a body 412, a lower foot 414 and an upper hood 415. The hood 415 operates to seat the implant at a precise depth regardless of the depth of the scleral incision, and resists scleral tissue growth over the implant. In order to easily distinguish the foot 414 from the hood 415, so that the implant 410 is implanted in the proper orientation, one or both of the foot and hood may be provided with distinguishing colors, textures, or other indicia.

Figure 16:
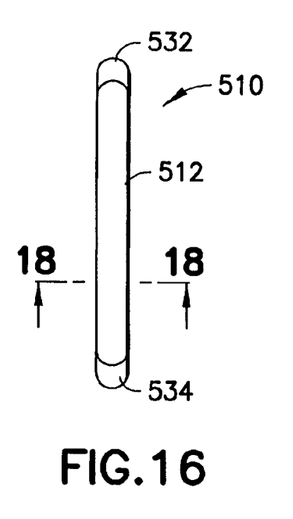
FIG. 16 is a top view of a fifth embodiment of a scleral implant according to the invention.
Figure 17:
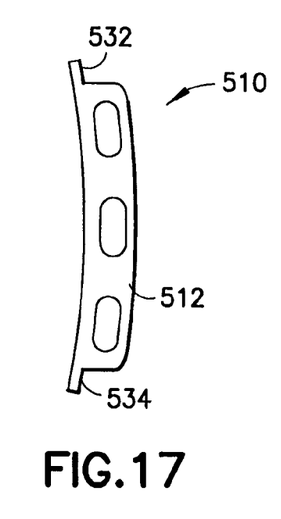
FIG. 17 is a side elevation of the scleral implant of FIG. 16.
Figure 18:
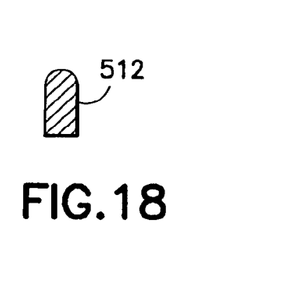
FIG. 18 is a cross-sectional shape defined by the scleral implant of FIG. 16 across line 18—18.
Figure 19:
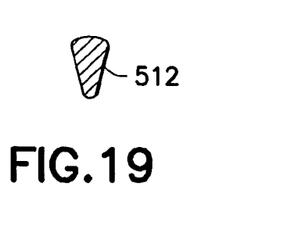
FIG. 19 is an alternate cross-sectional shape defined by the scleral implant of FIG. 16 across line 18—18.

Referring to FIGS. 16 and 17, a fifth embodiment of an implant 510 according to the invention is shown. Implant 510 has a body 512, but no laterally extending foot. Extensions 532 and 534 extend from the ends of the lower portion of the body 512. The implant may have several cross-sectional shapes across the body 512, such as generally rectangular (yet with slightly curved lower and/or upper sides) (FIG. 18) or generally triangular (FIG. 19). An implant with a triangular cross-section is best accommodated by the scleral incision.

Figure 20:
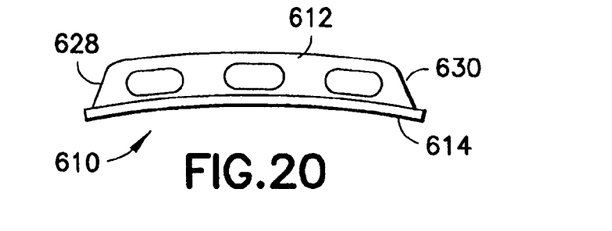
FIG. 20 is a side elevation view of a scleral implant according to a sixth embodiment of the invention.

Referring to FIG. 20, a sixth embodiment of an implant 610 is shown, substantially similar to the first embodiment 110. The ends 628, 630 of the body 612 slope downward towards a foot 614 of the implant. The downward slope allows the implant to anchor itself at each end in simple scleral incision that is not undercut lengthwise. Preferably, the scleral incision would be slightly shorter than with respect to the other embodiments, so that the ends 628, 630 of the implant would press into the scleral tissue and reduce the need for suture. More preferably, the implant may be constructed of a resilient material which can be compressed or bent upon implantation, and then released to automatically press into the scleral tissue and stabilize itself.

Each of the above described implants 210, 310, 410, 510 may be implanted generally as described above with respect to the first embodiment.

Figure 21:
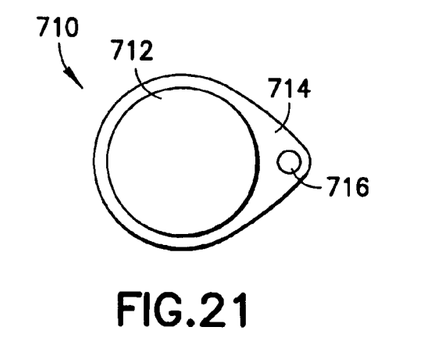
FIG. 21 is a plan view of a scleral implant according to a seventh embodiment of the invention.
Figure 22:
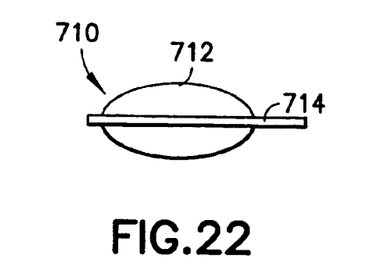
FIG. 22 is a side elevation view of the scleral implant of FIG. 21.

Turning now to FIGS. 21 and 22, a seventh embodiment of an implant 710 is shown. The implant 710 includes a generally disc-shaped bulbous body 712 with a tab 714 extending from a peripheral portion thereof. The tab 714 has a suture hole 716 through a portion thereof. The disc-shaped body 712 is preferably generally circular through a horizontal cross-section and generally ellipsoid through a vertical cross-section, though the body can be provided with another shape, e.g., teardrop, as well. The body preferably has a diameter of 2.0 to 3.5 mm. Preferably the body 712 and tab 714 together define a teardrop shape.

Figure 23:
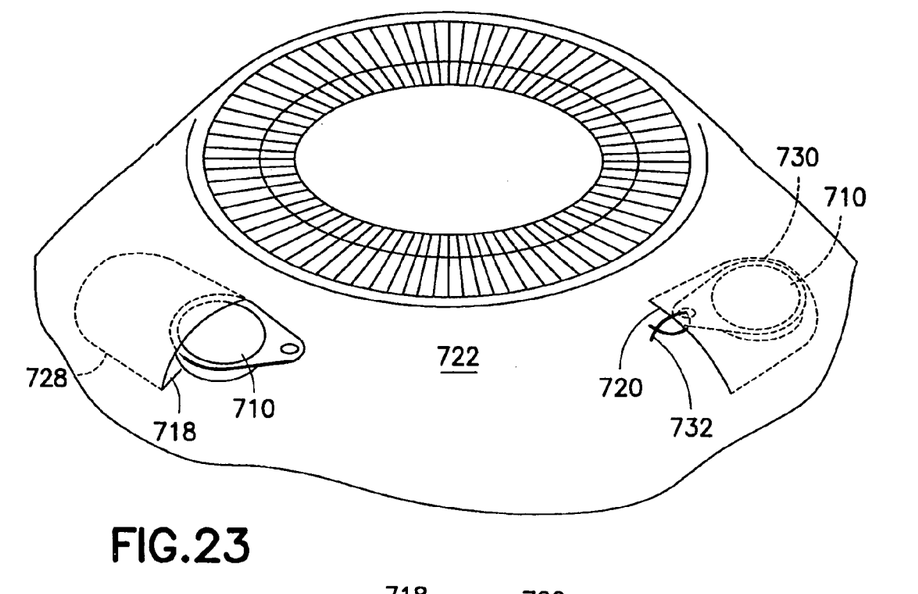
FIG. 23 illustrates a method of treating eye disorders according to the invention from a view looking down on an upper portion of the eye.
Figure 24:
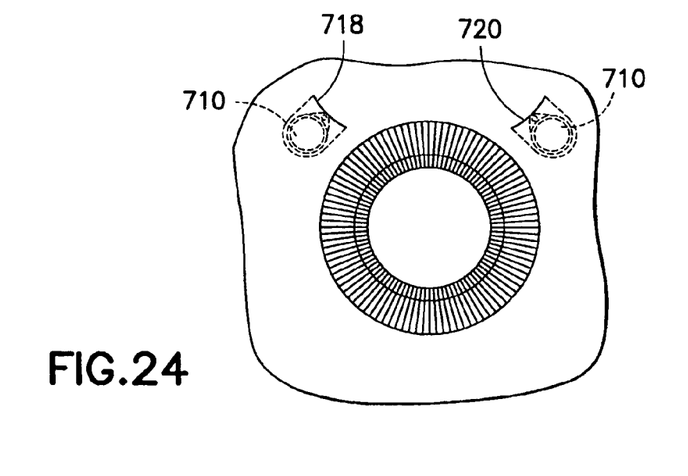
FIG. 24 shows the scleral implants of FIGS. 21 and 22 implanted according to the method of the invention.

Referring now to FIGS. 23 and 24, according to a method of the invention, two short straight or slightly curved incisions 718, 720 are made over the sclera 722 along an upper portion of the sclera, e.g., at eleven o'clock and one o'clock. Dissecting away from a twelve o'clock position, two pockets 728, 730 are defined at approximately 90% depth and slightly larger than the implants. For each pocket, an implant 710 is grasped with a forceps by its tab 714 and maneuvered into its respective pocket. Suture 732 is then optionally extended through the suture hole and used to close the incisions 718, 720 and substantially enclose the implants 710 within the pockets 728, 730. It is appreciated that because the implants are provided in pockets, sufficient capture of the implants may be provided without the use of the suture. In such cases, providing the implant 710 with a tab 714 having a suture hole 716 may not be necessary or even preferred. Moreover, as opposed to two implants, a single implant implanted through a single incision into a single pocket preferably located at approximately eleven o'clock or one o'clock may also provide substantially the same effect. Alternatively, more than two scleral pockets and/or other locations on the sclera can be used for insertion of the implant 710.

It is believed that the implanted implants 710 cause pressure to be applied to the ciliary body and/or onto the vitreous cavity, thus increasing the pressure that would be placed posteriorly on the crystalline lens and possibly moving it forward. It is also believed that there is also a degree of lifting to the overlying sclera, which may also effect additional space inside the eye for the ciliary body to contract. That is, the internal dynamics of the eye may be sufficiently altered to at least partially reverse or treat the effects of presbyopia. In addition to the treatment of presbyopia, it is recognized that the implant and methodology have application for the treatment of other eye disorders, including glaucoma. Furthermore, the implant may improve the ability to see small objects at near via other opthalmic and neurological mechanisms relating to accomodation and otherwise.

Figure 25:
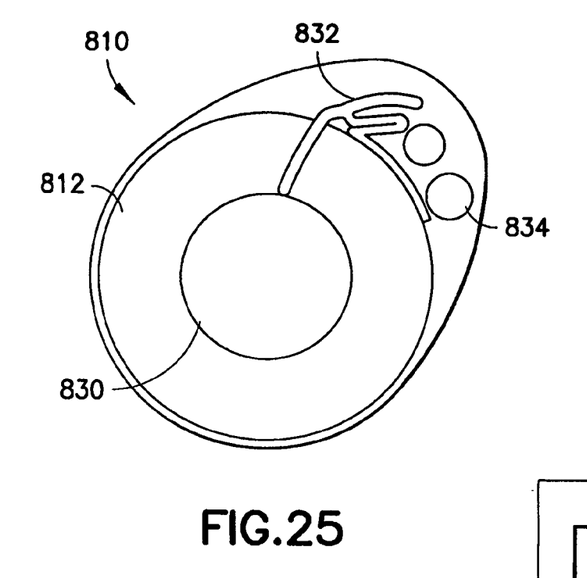
FIG. 25 is a bottom view of a scleral implant according to an eighth embodiment of the invention.
Figure 26:
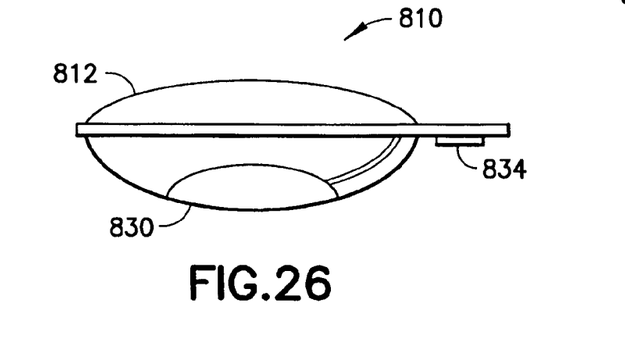
FIG. 26 is a side elevation view of the scleral implant of FIG. 21.
Figure 27:
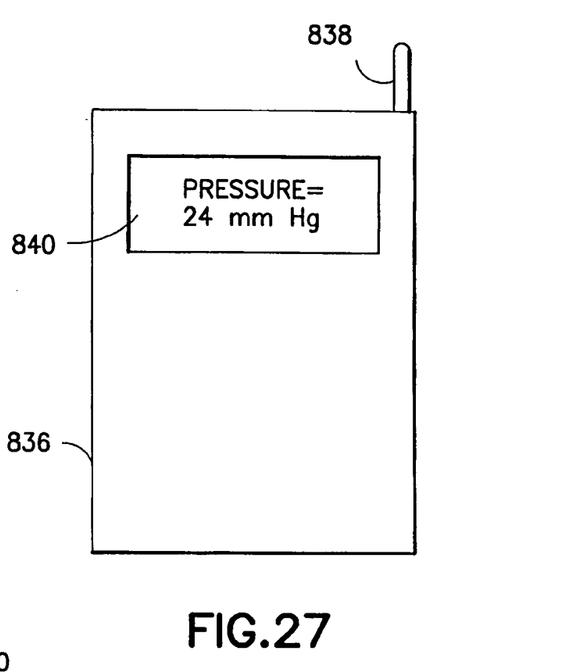
FIG. 27 is a schematic view of a receiver for communicating with the scleral implant of FIGS. 25 and 26.

Turning now to FIGS. 25 and 26, an implant 810 is provided with a pressure transducer 830, a transmitter 832 in communication with the transducer 830, and optionally a power source such as a body heat power source 834, described in U.S. Pat. No. 6,470,212 to Weijand, which is hereby incorporated by reference herein in its entirety. Though the implant shown is similar to the seventh embodiment 710, it can be of any shape suitable for scleral implantation, including the shapes in the prior art. The pressure transducer 830 is preferably coupled to a lower portion of the body 812 of the implant, or alternatively the entire implant (or a substantial portion of the implant) may be the pressure transducer. The pressure transducer 830 measures the intraocular pressure to which the implanted implant 810 is subject, and the transmitter 832 (antenna) transmits a reading of the pressure to a receiving device 836. Referring to FIG. 27, the receiving device 836 includes an antenna 838 for communicating with the transmitter 830 and a display that displays the measured pressure on a screen 840. The receiving device 836 is preferably locatable proximate the eye, but also preferably not in contact with the eye surface. If the implant 810 does not include a power source, the receiving device 836 may be adapted to power the transducer 830 through electromagnetic induction. Such a system (implant 810 and receiver 836) may be used to monitor how the eye pressure is affected for purposes of monitoring or modifying presbyopia treatment, glaucoma treatment, or any other eye disorder in which vitreous pressure is an important parameter.

Each of the above-described implants is made from a biocompatible material. For example, biodegradable and bioabsorbable materials may be used where the effects of the treatment are intended to be temporary. An expandable material (e.g., hydrophilic material) is preferably used to cause an increased volumetric expansion of the eye postoperatively. Exemplar expandable materials include crosslink polyethylene oxide, polyvinyl alcohol, silk-elastin copolymers. Furthermore, UV-cured crosslinked polymers such as polyethylene oxide hydrogels, agarose, cyanate ester-modified polymers, polyvinyl chloride, and diethyl fumarate/propylene fumarate, can also be used. Moreover, temperature sensitive materials, such as aliphatic polyesters such as those made from L,L-dilactide, diglycolide and p-dioxanone can also be used. In addition, a metal or metal alloy can also be used.

In addition, implants may be molded in situ to better match the implant to incision shape, using, e.g., hydrogels. That is, after forming the incision, the incision is physically opened and a hydrogel or other suitable fluid or otherwise conformable material is provided therein to substantially fill the incision. The material is then cured so that the implant matches the incision shape, and preferably even expands the incision, to provide the desired effect.

There have been described and illustrated herein several embodiments of scleral implants, as well as a method of scleral implant implantation for treatment of certain eye disorders. While particular embodiments of the invention have been described, it is not intended that the invention be limited thereto, as it is intended that the invention be as broad in scope as the art will allow and that the specification be read likewise. As such, several implants have been disclosed with particular configurations and structure, it is intended that the various aspects of the embodiments be combined to define yet other embodiments. It will therefore be appreciated by those skilled in the art that yet other modifications could be made to the provided invention without deviating from its spirit and scope as claimed.

What is claimed is:

1. A scleral implant for implantation into a pocket incised in a quadrant of the sclera of the eye, comprising:
   a) an ellipsoid body having a diameter of 2.0 to 3.5 mm and otherwise sized to be received in the pocket in the sclera; and
   b) a tab extending from said body, said tab defining a hole, wherein horizontal sections through said body define substantially circular shapes, and vertical sections through said body define substantially elliptical shapes.

2. A scleral implant for implantation into a pocket incised in a quadrant of the sclera of the eye, comprising:
   a) an ellipsoid body sized to be received in the pocket in the sclera; and
   b) a tab extending from said body, said tab defining a hole, wherein said body is made from an expandable material.

3. A scleral implant according to claim 2, wherein:
   said body has a diameter of 2.0 to 3.5 mm.

4. A scleral implant according to claim 2, wherein:
   horizontal sections through said body define substantially circular shapes, and vertical sections through said body define substantially elliptical shapes.

5. A scleral implant for implantation into the sclera of the eye, comprising:
   a) a biocompatible body having an ellipsoid shape and a longest dimension of approximately 2.0 to 3.5 mm and otherwise sized for insertion into the sclera of the eye, wherein horizontal sections through said body define substantially circular shapes, and vertical sections through said body define substantially elliptical shapes;
   b) a pressure transducer that is one of coupled to and incorporated into said body;
   c) a tab extending from a portion of said body, said tab defining an opening adapted to receive suture, and said body and said tab together defining a teardrop shape.

6. A scleral implant according to claim 5, further comprising:
   d) a transmitter in communication with said transducer, said transmitter being one of coupled to and incorporated into said body.

7. A system for determining an intraocular pressure, comprising:
   a) a scleral implant including,
      i) a biocompatible body having a longest dimension of approximately 2.0 to 3.5 mm and otherwise sized for insertion into the sclera of the eye, said body including a substantially ellipsoid shape, and a tab extending from a portion of said body, said tab and said body together defining a teardrop shape, and
      ii) a pressure transducer that is one of coupled to and incorporated into said body; and
   b) a device adapted to communicate with said scleral implant, said device including a display that indicates the intraocular pressure measured by the pressure transducer.

8. A system according to claim 7, further comprising:
   a transmitter that is one of coupled to and incorporated into said body of said scleral implant.

9. A scleral implant according to claim 8, further comprising:
   a power source for said transmitter.

10. A scleral implant for implantation into the sclera of the eye, comprising:
    a) a biocompatible body having a longest dimension of approximately 2.0 to 3.5 mm and otherwise sized and shaped for insertion into the sclera of the eye so that when so inserted said body causes distension of the sclera so as to result in a beneficial effect on at least one of intraocular pressure and presbyopia;
    b) a tab extending from a portion of said body, said tab and said body together defining a teardrop shape; and
    c) a pressure transducer that is one of coupled to and incorporated into said body.

11. A scleral implant according to claim 10, further comprising:
    d) a transmitter in communication with said transducer, said transmitter being one of coupled to and incorporated into said body.

12. A scleral implant according to claim 10, wherein:
    said body is substantially ellipsoid in shape.

13. A scleral implant according to claim 10, wherein:
    horizontal sections through said body define substantially circular shapes, and vertical sections through said body define substantially elliptical shapes.

* * * * *